(12) United States Patent
Huffstetler et al.

(10) Patent No.: US 10,551,316 B2
(45) Date of Patent: *Feb. 4, 2020

(54) FABRICATION OF A FLUORESCENT MATERIAL FOR SENSING AN ANALYTE

(71) Applicant: Senseonics, Incorporated, Germantown, MD (US)

(72) Inventors: Philip Huffstetler, Germantown, MD (US); Jeremy Emken, Germantown, MD (US); Todd Whitehurst, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/180,547

(22) Filed: Nov. 5, 2018

(65) Prior Publication Data
US 2019/0079009 A1  Mar. 14, 2019

Related U.S. Application Data

(60) Continuation of application No. 15/606,260, filed on May 26, 2017, now Pat. No. 10,119,911, which is a (Continued)

(51) Int. Cl.
*G01N 21/64* (2006.01)
*G01N 33/58* (2006.01)
(Continued)

(52) U.S. Cl.
CPC ......... *G01N 21/6428* (2013.01); *G01N 21/77* (2013.01); *G01N 33/544* (2013.01);
(Continued)

(58) Field of Classification Search
CPC .................. G01N 21/6428; G01N 33/582
See application file for complete search history.

(56) References Cited

U.S. PATENT DOCUMENTS

| 7,713,745 B2 | 5/2010 | Colvin, Jr. et al. |
| 8,694,069 B1 | 4/2014 | Kosa et al. |

(Continued)

OTHER PUBLICATIONS

Crooks, Patterning of Hyper-branched Polymer Films, Chemphyschem 2001, 2 644-654 (2001).*

(Continued)

*Primary Examiner* — Robert D Harlan
(74) *Attorney, Agent, or Firm* — Rothwell, Figg, Ernst & Manbeck, P.C.

(57) ABSTRACT

An analyte indicator may include a porous base and may be included in an analyte sensor. The analyte indicator may retain its physical, chemical, and optical properties in the presence of compression. The porous base may not vary in opacity. The analyte indicator may include (i) a polymer unit attached or polymerized onto or out of the porous base and (ii) an analyte sensing element attached to the polymer unit or copolymerized with the polymer unit. The analyte sensing element may include one or more indicator molecule. The analyte sensing element may include one or more indicator polymer chains. The analyte indicator may include (i) an indicator polymer chain attached or polymerized onto or out of the porous base and (ii) indicator molecules attached to the indicator polymer chain.

9 Claims, 8 Drawing Sheets

Related U.S. Application Data division of application No. 14/807,033, filed on Jul. 23, 2015, now Pat. No. 9,778,190.

(60) Provisional application No. 62/027,997, filed on Jul. 23, 2014.

(51) Int. Cl.
  G01N 33/544 (2006.01)
  G01N 21/77 (2006.01)
  G01N 31/22 (2006.01)

(52) U.S. Cl.
  CPC .......... G01N 33/582 (2013.01); G01N 31/22 (2013.01); *G01N 2021/773* (2013.01); *G01N 2021/7786* (2013.01)

(56) References Cited

U.S. PATENT DOCUMENTS 9,778,190 B2 * 10/2017 Huffstetler ............ G01N 21/77
2008/0008625 A1   1/2008 Thomas et al.
2014/0187878 A1   7/2014 Emken et al.

OTHER PUBLICATIONS

Richard M. Crooks, "Patterning of Hyperbranched Ploymer Films," Chemphyschem—A European Journal of Chemical Physics & Physicalchemistry, vol. 2, No. 11, pp. 644-654, XP055443525 (Nov. 19, 2001).

Dai Geun Kim et al., "A Glucose-Selective Fluorescent Water-Soluble Hyperbranched Polymer Sensor With Boronic Acid End Groups," Mol. Cryst. Liq. Cryst., vol. 519, No. 1, pp. 54-64, XP008156960 (Jan. 1, 2010).

* cited by examiner

FABRICATION OF A FLUORESCENT MATERIAL FOR SENSING AN ANALYTE

CROSS-REFERENCE TO RELATED APPLICATION

The present application is continuation of U.S. patent application Ser. No. 15/606,260, which was filed on May 26, 2017, and is a divisional of U.S. patent application Ser. No. 14/807,033, which was filed on Jul. 23, 2015, now U.S. Pat. No. 9,778,190, and claims the benefit of priority to U.S. Provisional Application Ser. No. 62/027,997, which was filed on Jul. 23, 2014, all of which are incorporated herein by reference in their entireties.

BACKGROUND

Field of Invention

The present invention relates to analyte indicators. Specifically, the present invention relates to an analyte indicator including an analyte sensing element attached to or copolymerized with a polymer unit or chain that is attached or polymerized onto or out of a porous base.

Discussion of the Background

Existing analyte indicators may vary in physical, chemical, and/or optical properties in the presence of compression, and the variation may reduce the sensitivity of sensors incorporating the existing analyte indicators. Moreover, existing analyte indicators may require a long period of time to hydrate. Accordingly, there is a need for an improved analyte indicator.

SUMMARY

One aspect of the invention may provide an analyte indicator, which may be included in an analyte sensor. The analyte indicator may include a porous base, a polymer unit, and an analyte sensing element. The polymer unit may be attached or polymerized onto or out of the porous base. The analyte sensing element may be attached to the polymer unit or copolymerized with the polymer unit.

In some embodiments, the porous base may not vary in opacity. In some embodiments, the analyte indicator may retain its physical, chemical, and optical properties in the presence of compression (e.g., from a membrane or other source). In some embodiments, the polymer unit may be hydrophilic or amphiphilic.

In some embodiments, the analyte sensing element may be one or more indicator molecule. In some embodiments, the analyte sensing element may include an indicator polymer chain. In some embodiments, the indicator polymer chain may include indicator molecules. In some embodiments, the analyte sensing element may include indicator polymer chains, and each of the indicator polymer chains of the analyte sensing element may include indicator molecules. In some embodiments, the indicator polymer chain may be hydrophilic or amphiphilic.

In some embodiments, the analyte indicator may include a second polymer unit and a second analyte sensing element. The second polymer unit may be attached or polymerized onto or out of the porous base. The second analyte sensing element may be attached to the second polymer unit or copolymerized with the second polymer unit. In other embodiments, the analyte indicator may include a third or more polymer units and a third or more analyte sensing elements.

Another aspect of the invention may provide an analyte indicator, which may be included in an analyte sensor. The analyte indicator may include a porous base, an indicator polymer chain, and indicator molecules. The indicator polymer chain may be attached or polymerized onto or out of the porous base. The indicator molecules may be attached to the indicator polymer chain.

In some embodiments, the porous base may not vary in opacity. In some embodiments, the analyte indicator may retain its physical, chemical, and optical properties in the presence of compression (e.g., from a membrane or other source). In some embodiments, the polymer unit may be hydrophilic or amphiphilic.

In some embodiments, a porous membrane may be wrapped tightly over the analyte indicator.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1A:
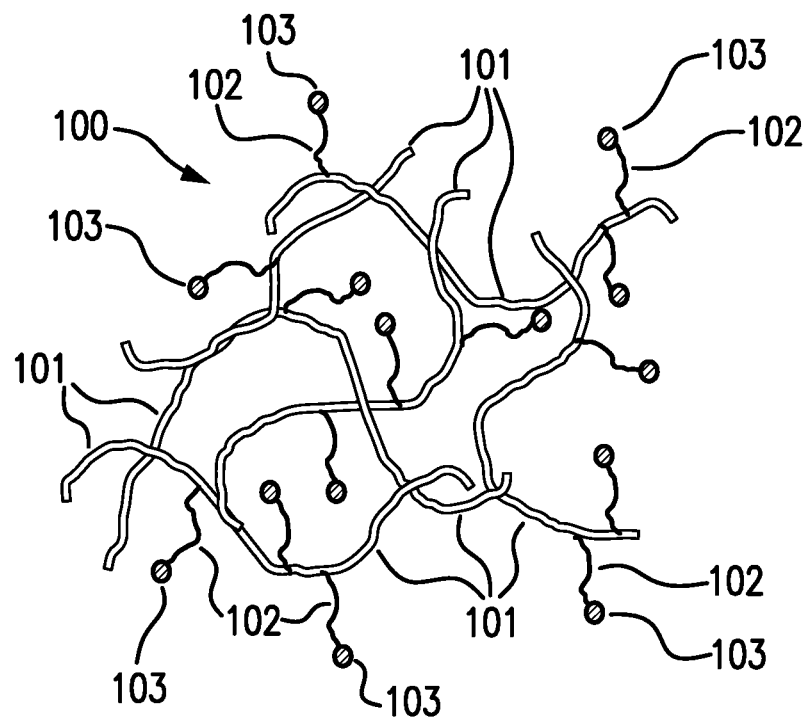
FIG. 1A is a macroscale interpretation of an analyte indicator embodying aspects of the present invention in which polymer units are attached to the porous base and then modified to contain either an indicator molecule or one or more indicator polymer chains yielding a branched system.

Analyte systems in accordance with embodiments of the present invention may include an analyte sensor and a transceiver. In some embodiments, the analyte system may be a continuous analyte monitoring system. In some non-limiting embodiments, the system may be 24-hour continuous analyte monitoring system configured to measure analyte levels. In one non-limiting embodiment, the continuous analyte monitoring system may be a continuous glucose monitoring system (CGMS) and may measure interstitial fluid glucose levels in adults who have diabetes mellitus.

In some embodiments, the analyte sensor may be a subcutaneously implantable sensor (e.g., in the back of the upper arm, wrist, or lower abdomen) with no sensor part protruding from the skin, and the transceiver may be a battery-powered transceiver configured to wirelessly receive data from the analyte sensor (e.g., via inductive communication) and function as a data collection and monitoring device. However, this is not required, and, in alternative embodiments, the analyte sensor may be a transcutaneous sensor having a wired connection to the transceiver. In some embodiments, the transceiver sends data to a smartphone (or other device, such as a receiver, laptop, or personal computer). The smartphone may execute a medical application (e.g., a mobile medical application).

In some embodiments, the analyte sensor may be encased in a biocompatible material. In some embodiments, the sensor utilizes a fluorescent, analyte-indicating macromolecule. In some embodiments, the sensor may last up to 6 months and may be replaced thereafter. In some embodiments, the sensor may include a light source (e.g., light emitting diode). The sensor may include a polymer. The light source may excite the polymer, and the polymer may rapidly signal changes in analyte concentration via a change in light output, which may be measured by the sensor (e.g., by a photodetector of the sensor). In some embodiments, the sensor relays the measurement to the transceiver. In some embodiments, the entire measurement may be done autonomously and independently without any prompting by the user.

In some embodiments, the fluorescent analyte chemistry is not subject to instabilities intrinsic to current protein-based analyte sensors. For instance, in some embodiments, the analyte measurement by the sensor neither consumes chemicals (e.g., oxygen, glucose) nor forms chemicals (e.g., hydrogen peroxide). Consequently, sensors in accordance with embodiments of the invention may be inherently more stable and accurate, and an implanted sensor may last for up to 6 months or longer before being replaced.

In some embodiments, the analyte-indicating polymer of the analyte sensor may include indicator molecules, such as, for example and without limitation, any of the indicator molecules described in U.S. Patent Application Publication No. 2014/0088383, which is incorporated by reference in its entirety. In some non-limiting embodiments where the analyte monitoring system is a glucose monitoring system, the indicator molecules may be fluorescent indicator molecules that reversibly bind glucose. In one non-limiting embodiment, when a fluorescent indicator molecule has bound glucose, then the indicator molecule becomes fluorescent, in which case it absorbs (or is excited by) light at a wavelength of approximately 378 nm and emits light in the range of 400 to 500 nm. When no glucose is bound, then the indicator molecule may be only weakly fluorescent. In a non-limiting embodiment, the indicator molecules may be embedded in a polymer graft that covers only a small portion of the sensor.

In some existing "hydrogel" embodiments, the polymer graft may be a "hydrogel" containing three monomers: (i) the TFM fluorescent indicator, (ii) hydroxyethylmethacrylate (HEMA), which is a methacrylate, and (iii) polyethylene glycol diacrylate (PEG-diacrylate). The three monomers may be in specific molar ratios. For example, in one hydrogel embodiment, the fluorescent indicator may comprise 0.1 molar percent, HEMA may comprise 94.3 molar percent, and PEG may comprise 5.6 molar percent. The PEG may act as a cross-linker and create a sponge-like matrix/gel. The PEG may increase hydrophilicity. In some embodiments, the hydrogel polymer graft may be synthesized using conventional free radical polymerization techniques.

In these existing hydrogel embodiments, the hydrogel polymer graft may be a sponge-like substance and, therefore, sensitive to mechanical damage and opacity changes. If the hydrogel polymer graft is put directly in contact with body tissues, the indicator component may be rapidly oxidized, which limits the lifetime of the analyte sensor. In addition, if a membrane (e.g., a nylon membrane) is placed over the hydrogel graft (i.e., between the hydrogel graft and the body tissues), the membrane may compress the hydrogel graft, and, as a result, the hydrogel may be incapable of expanding to its original state. The compression by the membrane placed over the hydrogel may change the hydrogel's opacity or ability to scatter the fluorescent signal efficiently back to photodetector(s) (e.g., photodiode(s)) of the analyte sensor, reducing the sensor's sensitivity and optical stability. Therefore, if the membrane fits too snugly around the hydrogel, the sensor's sensitivity may be reduced. Additionally, if the membrane is not snug, then the hydrogel may still degrade, or the analyte (e.g., glucose) may take too long to diffuse into the hydrogel, making the sensor less responsive. Furthermore, bulk hydrogel may require days to fully hydrate, which imposes an undesired wait time limitation on the product use. Moreover, the bulk hydrogel is opaque (white), and that opacity can be affected by solute (e.g., by the protein concentration in the solute), which may affect the in vivo analyte accuracy of the sensor. Further, when the hydrogel is compressed, it cannot fully hydrate to its whitest state and will remain translucent or opalescent based on how much compression is placed onto the hydrogel, and this would add a significant amount of error into the analyte measurement.

Some embodiments of the present invention may provide an analyte indicator to replace the hydrogel system and address one or more issues (e.g., variation in physical, chemical, and/or optical properties of the hydrogel in the presence of compression and/or variation in the opacity of the hydrogel (white to clear) that can change the hydrogel's ability to scatter the signal back into the sensor). Moreover, in some embodiments, the analyte indicator may have a short hydration time (e.g., minutes) as opposed to the hours to days required for the hydrogel.

FIG. 1A illustrates an analyte indicator 100 embodying aspects of the present invention. In some embodiments, the analyte indicator 100 may include a porous base membrane layer 101. In some non-limiting embodiments, the porous base 101 may be comprised of nylon (e.g., Nylon 6, 6). However, this is not required, and, in some alternative embodiments, the porous base 101 may be comprised of other, similar membrane materials, such as, for example and without limitation, cellulose acetate, polypropylene, polyether sulfone, polyethylene, polyvinylidene difluoride (PVDF), polycarbonate, polytetrafluoroethylene (PTFE), or polyethylene terephthalate (PET). In some non-limiting embodiments, the base membrane layer 101 does not vary in opacity. In some non-limiting embodiments, the porous base 101 may retain its physical, chemical, and optical properties in the presence of compression. As illustrated in FIG. 1A, in some embodiments, the base membrane layer 101 may include long, connected strands.

In some embodiments, as illustrated in FIG. 1A, the analyte indicator 100 may include a polymer 102 attached or polymerized onto or out of the porous base 101. In some embodiments, the polymer 102 may be in units (e.g., strands) that are attached to or polymerized off of the backbone provided by the base membrane layer 101. In some non-limiting embodiments, the polymer 102 may be polyethylene glycol (PEG). However, this is not required, and, in alternative embodiments, other materials may be used, such as, for example and without limitation, poly(oxazolines), poly(acrylamides), poly(electrolytes), poly(ethers), poly(vinyl pyrolidone), Poly(ethylenimines), poly(vinyl alcohol), poly(acrylates and methacrylates), and/or poly(maleic anhydride). The polymer units 102 may provide a flexible structure that retains its physical, chemical, and/or optical properties when compressed. In some embodiments, the polymer units may be hydrophilic or amphiphilic. In FIG. 1A, the polymer units 102 are shown as short strands off of the long strands of the base membrane layer 101.

In some embodiments, the analyte indicator 100 may include one or more analyte sensing elements 103. The one or more analyte sensing elements 103 may be attached or copolymerized to the polymer units 102. In some non-limiting embodiments, as illustrated in FIG. 1A, each polymer unit 102 may have one analyte sensing element 103 attached or copolymerized thereto. However, this is not required, and, in some alternative embodiments, one or more of the polymer units 102 may not have an analyte sensing element 103 attached or copolymerized thereto. For example, in one non-limiting alternative embodiment, a small number of analyte sensing elements 103 may be attached to the polymer units 102 (e.g., an analyte sensing element 103 may be attached to approximately one tenth of the polymer units 102). Moreover, in some alternative embodiments, one or more of the polymer units 102 may have multiple (e.g., two, three, four or more) analyte sensing elements 103 attached or copolymerized thereto. In FIG. 1A, the analyte sensing elements 103 are shown as circles attached or copolymerized to the polymer units 102.

Figure 1B:
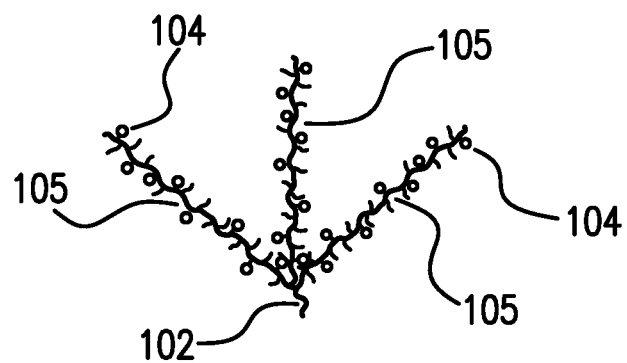
FIG. 1B is a blown-up view of a polymer unit containing indicator polymer chains embodying aspects of the present invention.

In some embodiments, one or more of the analyte sensing elements 103 may consist of one or more indicator molecules 104 attached to a polymer unit 102. In some embodiments, as illustrated in FIG. 1B, one or more of the analyte sensing elements 103 may include one or more indicator polymer chains (i.e., linear chains) 105 attached or polymerized onto or out of a polymer unit 102. In this way, the indicator polymer chains 105 may branch out from the polymer units 102. Accordingly, in some embodiments, the analyte indicator 100 may have a branched polymer structure. The indicator polymer chains 105 may include one or more indicator molecules 104 attached thereto. Although FIG. 1B illustrates an analyte sensing element 103 having three indicator polymer chains 105 attached or polymerized onto or out of a polymer unit 102, this is not required, and, in some alternative embodiments, an analyte sensing element 103 may have a different number (e.g., one, two, four, five, etc.) of indicator polymer chains 105 attached or polymerized onto or out of a polymer unit 102. In some embodiments, although not illustrated in FIG. 1B, one or more of indicator polymer chains 105 may have one or more indicator polymer chains 105 attached or polymerized onto or out of the indicator polymer chain 105 for additional branching.

In some non-limiting embodiments, the indicator polymer chains 105 may be short (e.g., 1-200 nm). In some embodiments, the overall structure of the analyte indicator 100 including the one or more indicator polymer chains 105 retains its physical, chemical, and/or optical properties in the presence of compression from an external source (e.g., a secondary membrane wrapped on top of the analyte indicator). In some embodiments, the polymer chains 105 could consist of, for example and without limitation, 2-hydroxyethylmethacrylate, poly(ethylene glycol) methacrylate, acrylic acid, methacrylic acid, [2-(methacrylolyloxy)ethyl] dimethyl-(3-sulfopropyl)ammonium hydroxide, or vinyl pyrrolidone. However, in some alternative embodiments, other materials may be used for the polymer chains. In some embodiments, the indicator polymer chains 105 may be hydrophilic or amphiphilic.

In some non-limiting embodiments, the analyte indicator 100 may be formed by making the polymer chain(s) 105 with the indicator molecules 104 attached thereto and then attaching polymer chain(s) 105 to the polymer unit(s) 102, which may be already be attached or polymerized onto or out of the porous base 101. However, this is not required, and, in alternative embodiments, the analyte indicator 100 may be formed in different manners.

Figure 2A:
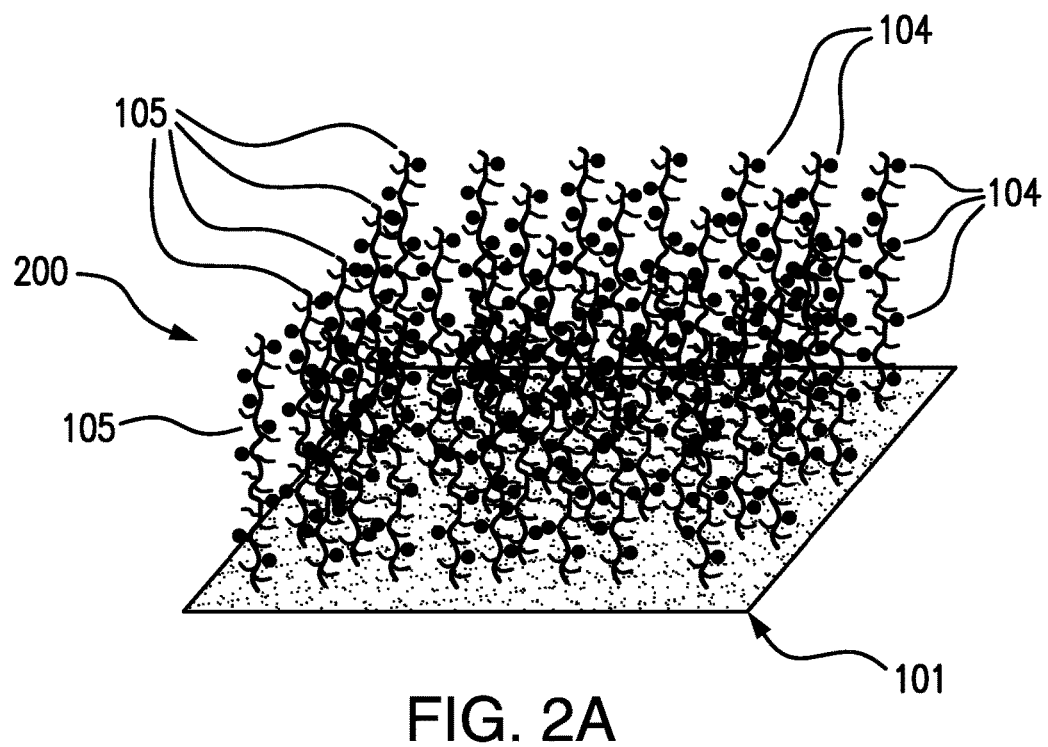
FIG. 2A illustrates an analyte indicator embodying aspects of the present invention in which one or more indicator polymer chains are attached or polymerized onto or out of a base membrane layer.

FIG. 2A illustrates an analyte indicator 200 embodying aspects of the present invention. Similar to the analyte indicator 100 illustrated in FIG. 1A, the analyte indicator 200 may include a porous base membrane layer 101. The analyte indicator 200 may include one or more indicator polymer chains 105 attached or polymerized onto or out of the base membrane layer 101. Accordingly, the analyte indicator 200 may have a linear polymer structure.

Figure 2B:
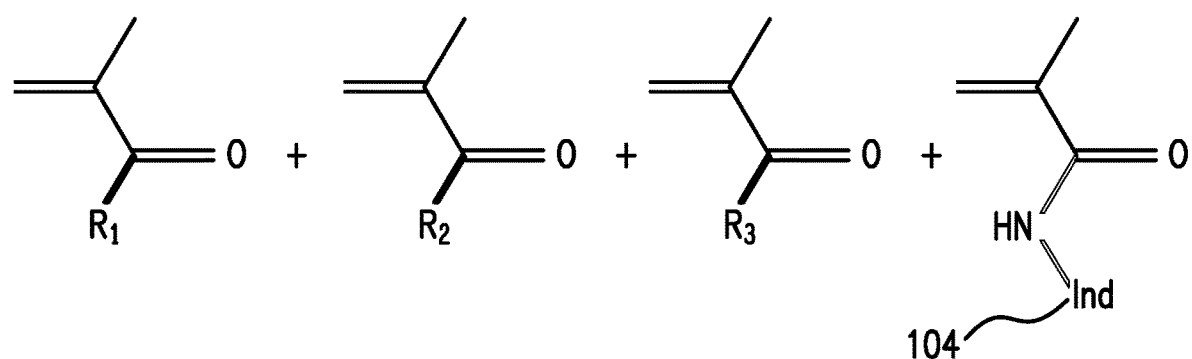
FIG. 2B shows the base monomer make-up of a grafted linear copolymer in which $R_1$, $R_2$, and $R_3$ are hydrophilic acrylate-based monomers such as but not limited to 2-hydroxyethyl methacrylate (HEMA), poly(ethylene glycol) methacrylate (PEGMA), and/or acrylic/methacrylic acid embodying aspects of the present invention.
Figure 3A:
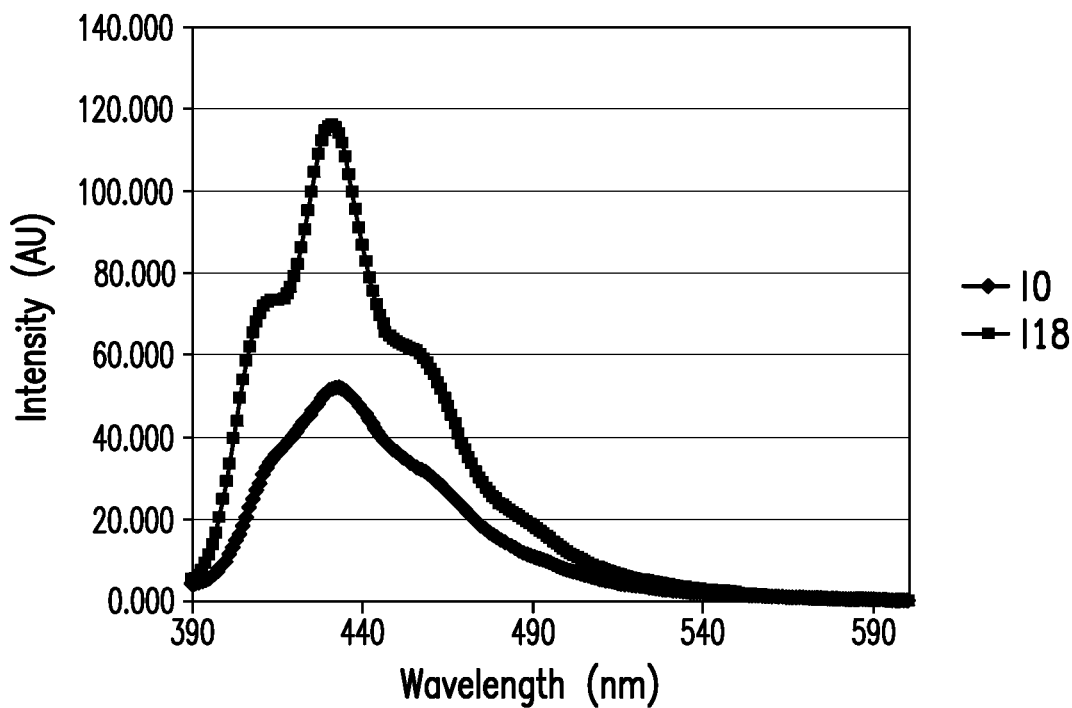
FIGS. 3A and 3B are graphs showing the emission light intensity and response time, respectively, of an analyte indicator embodying aspects of the present invention.
Figure 3B:
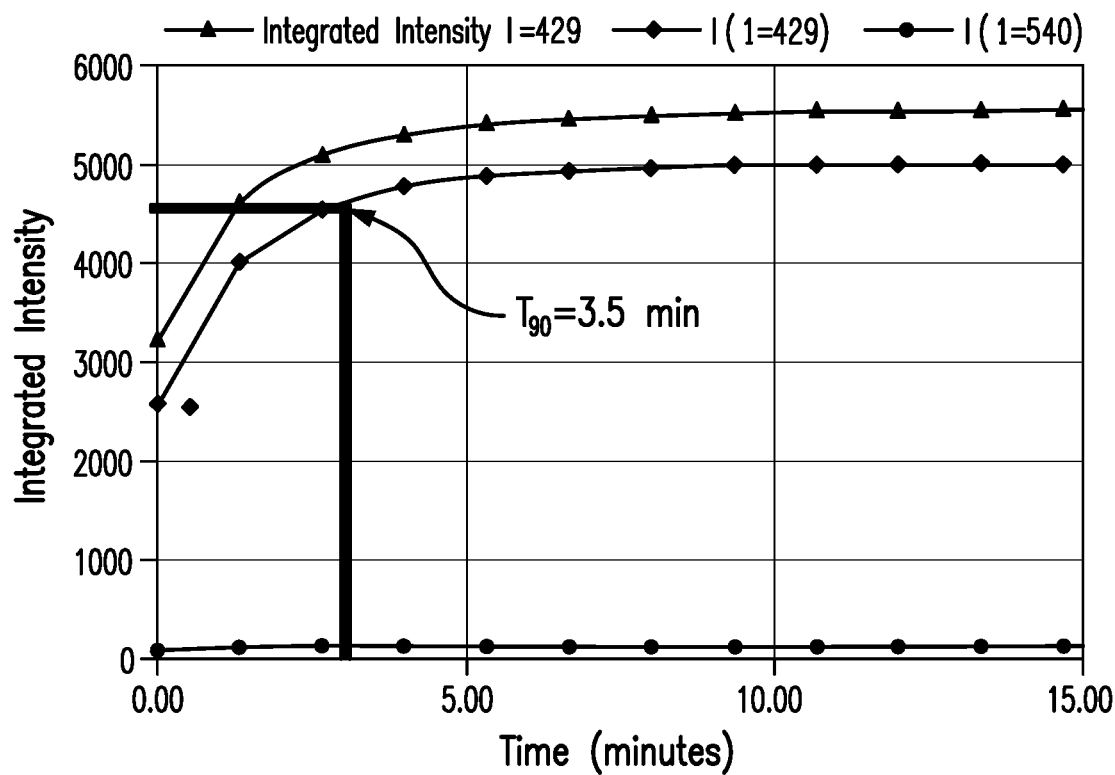
Figure 4A:
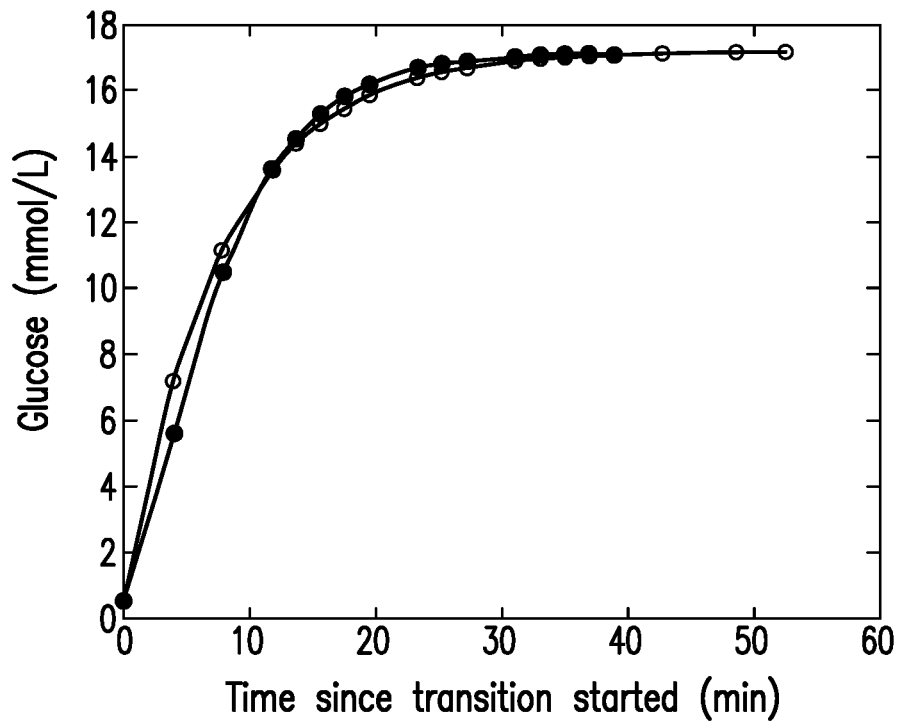
FIGS. 4A and 4B are graphs comparing glucose response curves of a hydrogel analyte indicator with the response time of an analyte indicator embodying aspects of the present invention, respectively.
Figure 4B:
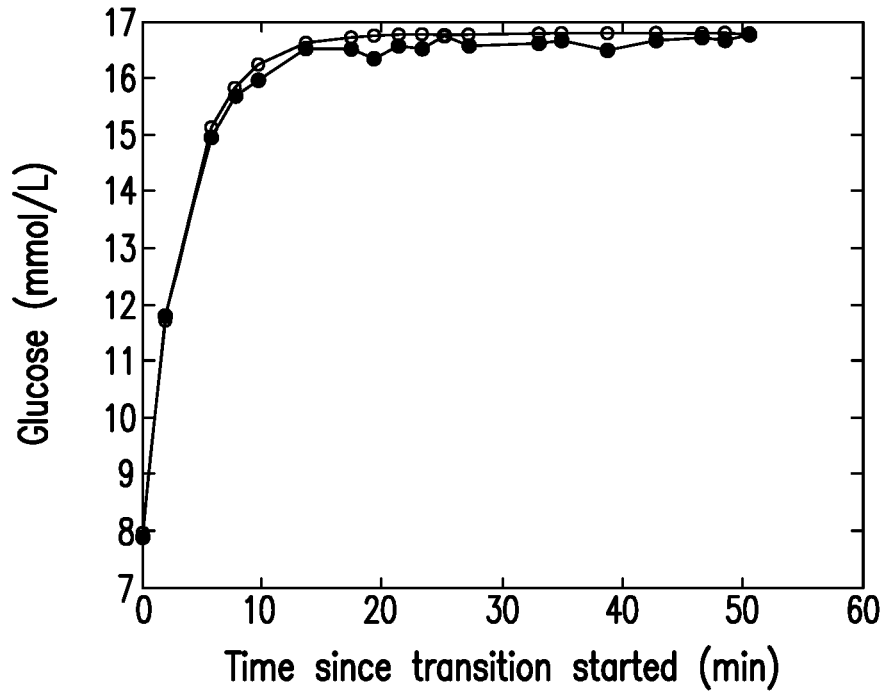

In some embodiments, as illustrated in FIG. 2A, the linear polymer chains 105 may be grafted onto a surface of the base membrane layer 101. FIG. 2B shows the base monomer make-up of a grafted linear copolymer 105. In some embodiments, $R_1$, $R_2$, and $R_3$ may be hydrophilic acrylate-based monomers such as but not limited to 2-hydroxyethyl methacrylate (HEMA), poly(ethylene glycol) methacrylate (PEGMA), and/or acrylic/methacrylic acid. In some non-limiting embodiments, the indicator polymer chains 105 of the analyte indicator 100 illustrated in FIG. 1B may have the base monomer make-up illustrated in FIG. 2B.

In some non-limiting embodiments, the analyte indicator 200 may be formed by making the polymer chain(s) 105 with the indicator molecules 104 attached thereto and then attaching polymer chain(s) 105 to the porous base 101. However, this is not required, and, in alternative embodiments, the analyte indicator 200 may be formed in a different manner.

In some embodiments, the indicator material (e.g., fluorescent indicator material) is hydrophilic, amphiphilic, and/or optically stable. In some embodiments, the analyte indicator (e.g., analyte indicator 100, which may have a branched polymer structure, or analyte indicator 200, which may be a linear copolymer graft membrane) may be wrapped tightly within a secondary membrane-based system without variance of the physical, chemical, and optical properties of the analyte indicator in the presence of substantial compression of the analyte indicator by the secondary membrane-based system. In some non-limiting embodiments, additional materials could also be tightly wrapped around the analyte indicator without interfering with the analyte indicator's properties. The additional materials may provide different layers, such as, for example, a layer of porous material to protect the analyte indicator from degradation and/or another layer of a dark material to make the sensor less sensitive to ambient light. In some embodiments, the analyte (e.g., glucose) may flow freely through the material, as the material may be hydrophilic and porous.

In some embodiments, the analyte indicator may be attached to the analyte sensor by $O_2$ plasma treating the sensor followed by tack welding the analyte indicator to the sensor at 450° F. (230° C.). However, this is not required, and, in alternative embodiments, the analyte indicator may be attached to the analyte sensor using a different method. In some embodiments, analyte indicator is attached to the sensor in a manner that allows intimate contact of the analyte indicator (e.g., analyte indicator 100, which may have the branched polymer structure, or analyte indicator 200, which may be a linear copolymer graft membrane) with the encasement (e.g., the PMMA encasement) of the sensor platform (e.g., by cutting the analyte indicator to 0.18"×0.47" when used with a sensor undercut width of 0.193").

In some embodiments, the analyte indicator (e.g., analyte indicator 100, which may have the branched polymer structure, or analyte indicator 200, which may be a linear copolymer graft membrane) has one or more of the following advantages: (i) ability to be produced on a large scale and stored, (ii) elimination of hydration before implant (i.e., allows for dry implant), (iii) retention of its physical, chemical, and optical properties in the presence of compression, (iv) optical stability, (v) built-in oxidative stability, (vi) fast response times, and (vii) a tuneable $K_d$.

In one non-limiting embodiment, the analyte indicator showed a modulation (e.g., 80-190%) equivalent to and greater than the modulation of the hydrogel system (e.g., 70-90%) as well as good to excellent $T_{90}$ response time data (e.g., 3.5 to 5 min) compared with the $T_{90}$ response time of the hydrogel system having nylon (e.g., 8.6±1.0 min). See FIGS. 3A, 3B, 4A, and 4B.

In one non-limiting embodiment, the analyte indicator may have a Tau value of 7±2 minutes. In one non-limiting embodiment, the analyte indicator has an average Tau of 9 minutes (9.5 minutes with PET) compared with an average Tau value of 17 minutes for the hydrogel wrapped with nylon. See FIG. 4.

In some embodiments, the analyte indicator may have tunable Kd values. For example, in non-limiting embodiment, an analyte indicator formulation may have a targeted $K_d$ of 15 and an actual $K_d$ of 13.7±0.4, a targeted $K_d$ of 18 and an actual $K_d$ of 17±1.3, a targeted $K_d$ of 20 and an actual Kd of 21, or a targeted Kd of 22 and an actual $K_d$ of 23±0.7.

In some embodiments, absolute modulation may be on the same scale as the hydrogel chemistry but with a lower $S_0$ allowing for the sensitivity of the gain to be adjusted to be less sensitive towards ambient light.

Figure 5:
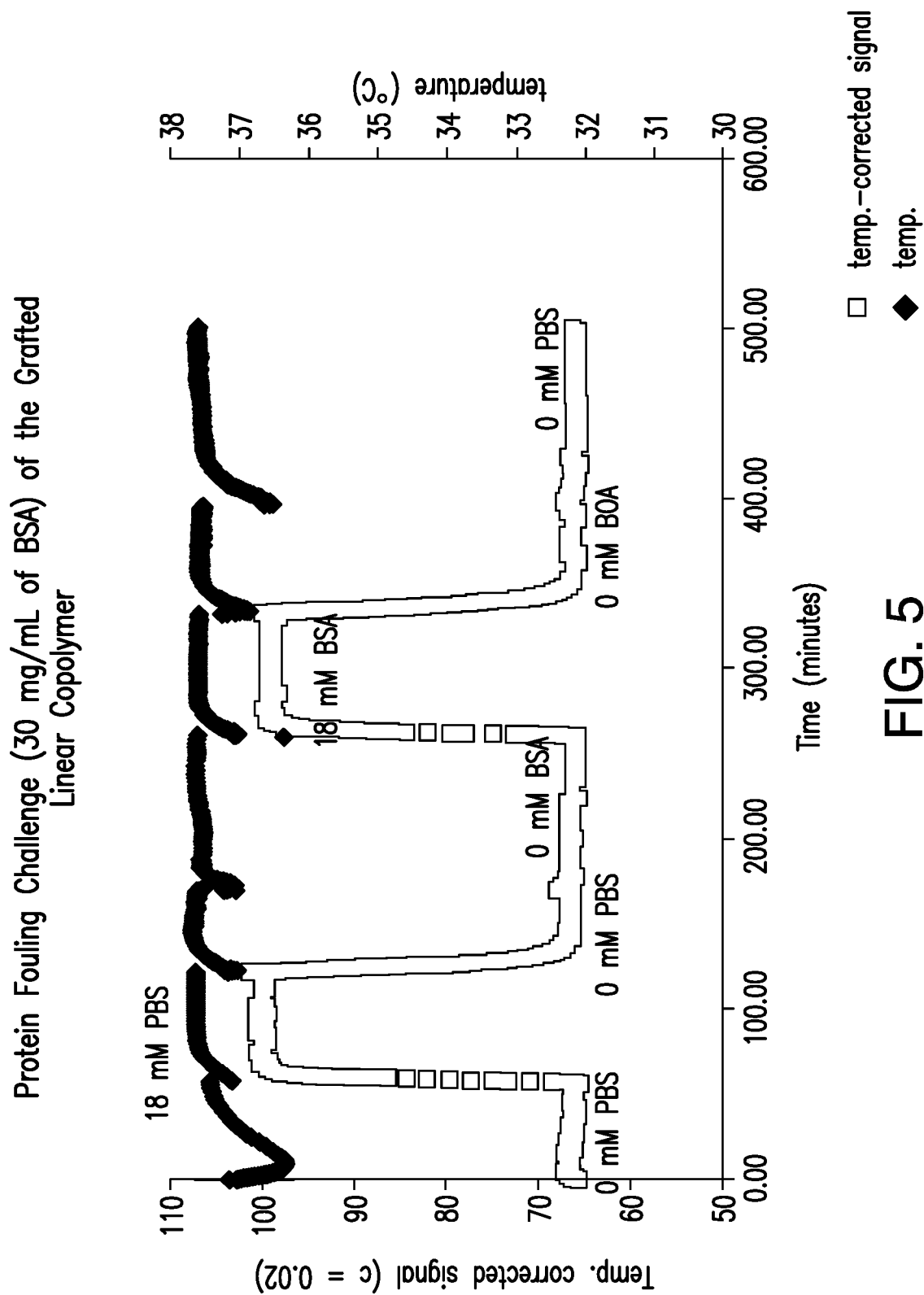
FIG. 5 is graph showing signal performance of an analyte indicator embodying aspects of the present invention in the presence of 30 mg/ml protein.
Figure 6:
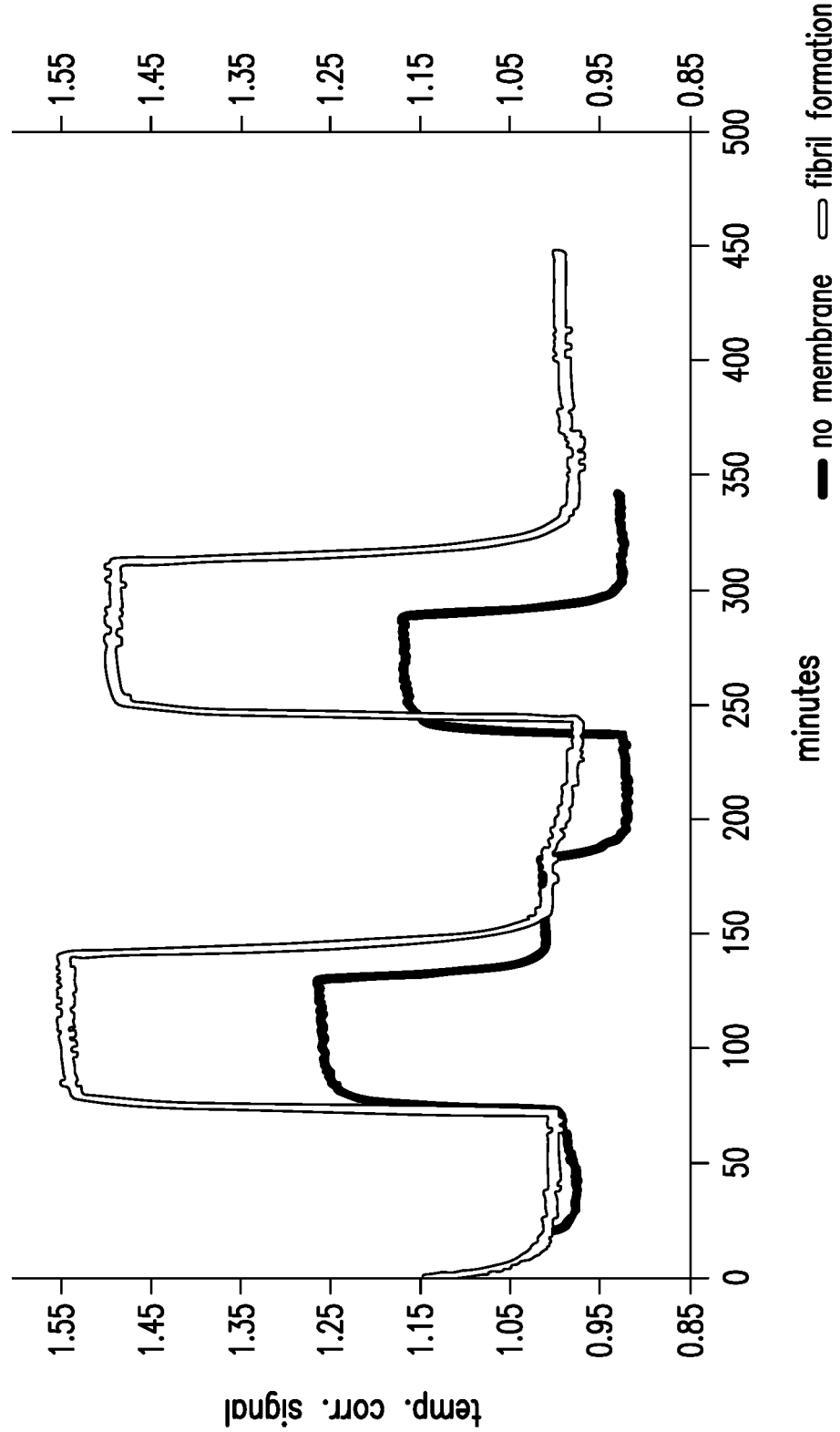
FIG. 6 is graph comparing of an analyte indicator embodying aspects of the present invention in the presence of protein to a hydrogel analyte indicator as a function of high (70 mg/mL) protein fouling.

In some embodiments, the sensor having the analyte indicator (e.g., analyte indicator 100 or 200) shows no drop in signal/sensor performance in the presence of bovine serum albumin (BSA) at a concentration of 30 mg/mL. See FIG. 5. FIG. 6 is a chart showing experimental results comparing one embodiment of the analyte indicator to the hydrogel system as a function of protein fouling at 70 mg/mL.

In some embodiments, rehydration of the analyte indicator (e.g., the linear copolymer graft membrane system) occurs quickly (e.g., in one non-limiting embodiment, the analyte sensor may take less than 5 minutes to reach a stable signal) compared to the nylon-wrapped hydrogel system, which requires 2-2.5 hours of rehydration for the nylon-wrapped hydrogel to reach a stable signal.

Figure 7:
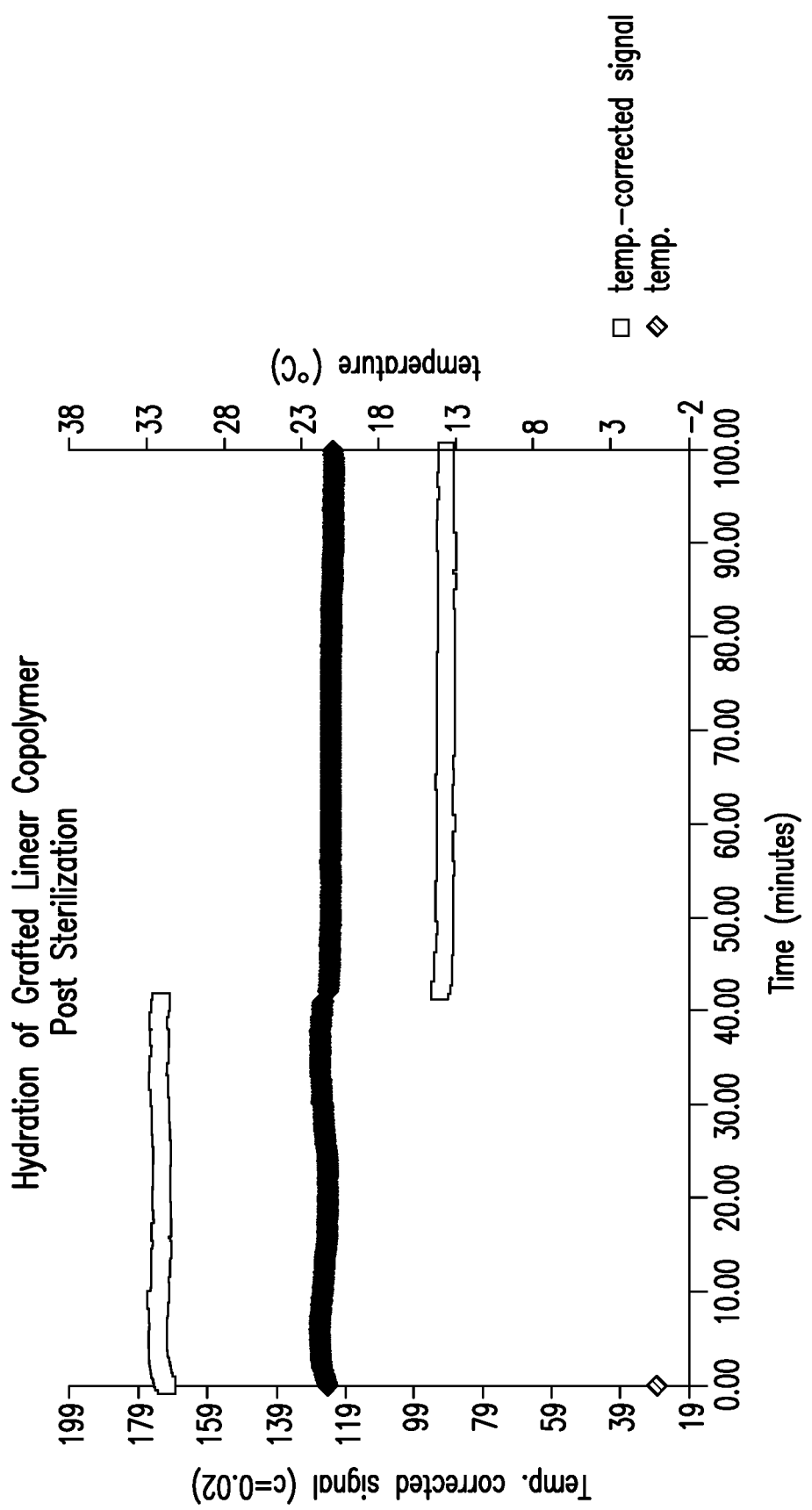
FIG. 7 is a graph showing the time required for post-sterilization hydration of an analyte sensing substrate embodying aspects of the present invention in saline.
Figure 8:
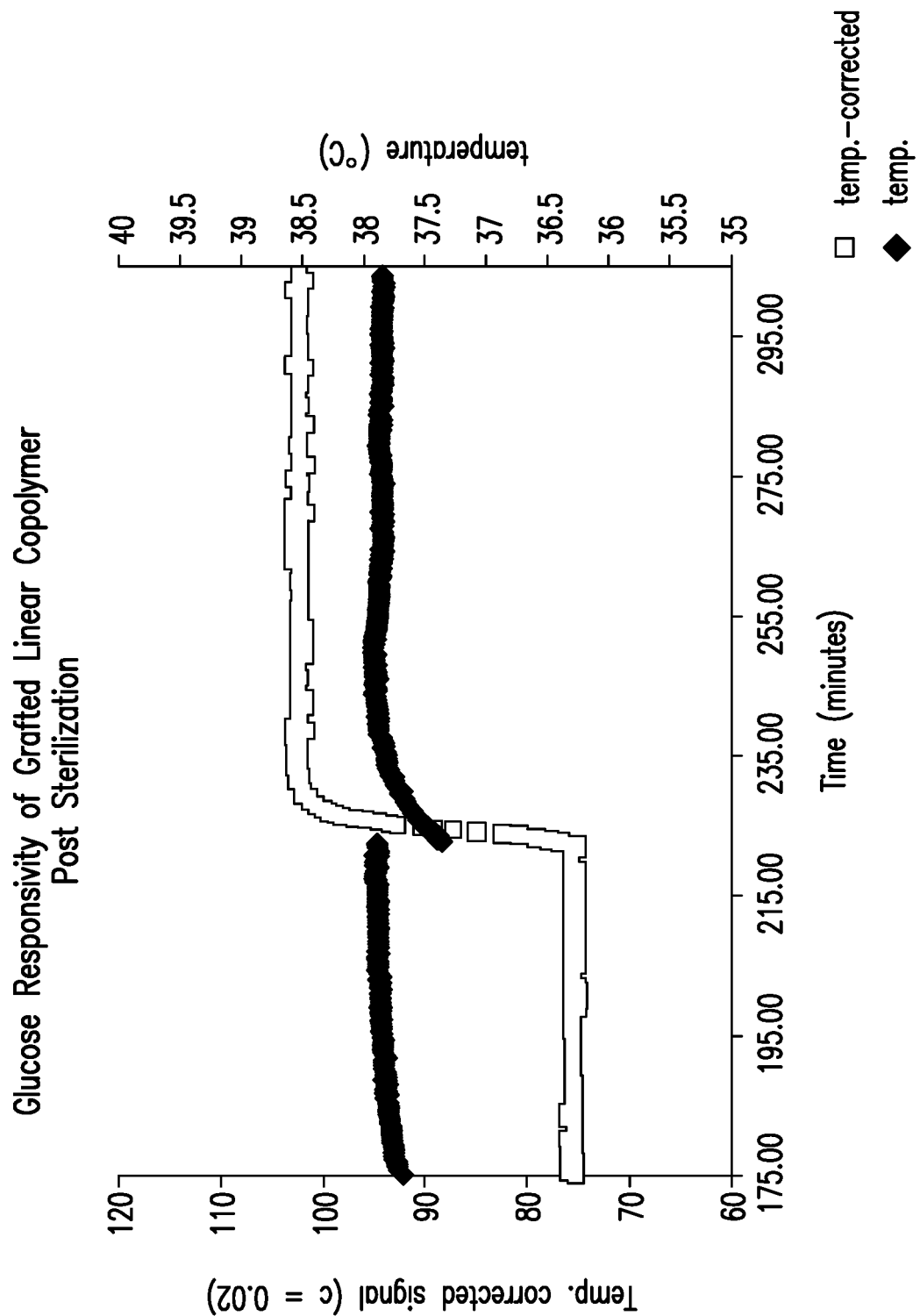
FIG. 8 is a graph showing post-ethylene oxide (ETO) sterilization glucose responsivity of an analyte indicator embodying aspects of the present invention.

In some non-limiting embodiments, the analyte indicator is sterilized (e.g., using ethylene oxide (ETO)), and a stable signal may be reached after approximately four minutes of post-sterilization hydration by dipping the sensor in saline solution. See FIG. 7. In some non-limiting embodiments, the analyte indicator (e.g., the linear copolymer graft membrane system) may have a $T_{90}$ response time of 4.8±0.3 minutes post-ETO sterilization. See FIG. 8.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:
1. An analyte indicator comprising:
a porous base;
a polymer unit polymerized onto or out of the porous base, wherein the polymer unit is a polyethylene glycol (PEG) unit; and
an analyte sensing element attached to the polymer unit or copolymerized with the polymer unit, wherein the analyte sensing element includes an indicator polymer chain attached or polymerized onto or out of the polymer unit and indicator molecules attached to the indicator polymer chain, the indicator molecules neither consume glucose nor form hydrogen peroxide, and the indicator polymer chain consists of 2-hydroxyethylmethacrylate, poly(ethylene glycol) methacrylate, acrylic acid, methacrylic acid, [2-(methacrylolyloxy) ethyl]dimethyl-(3-sulfopropyl)ammonium hydroxide, or vinyl pyrrolidone.
2. The analyte indicator of claim 1, wherein the analyte indicator retains its physical, chemical, and optical properties in the presence of compression.
3. The analyte indicator of claim 1, wherein the porous base does not vary in opacity.
4. The analyte indicator of claim 1, wherein the polymer unit is hydrophilic or amphiphilic.
5. The analyte indicator of claim 1, wherein the analyte sensing element comprises indicator polymer chains, and each of the indicator polymer chains of the analyte sensing element comprises indicator molecules.
6. The analyte indicator of claim 1, wherein the indicator polymer chain is hydrophilic or amphiphilic.
7. The analyte indicator of claim 1, wherein the base comprises nylon, cellulose, cellulose acetate, polypropylene, polyethylene, poly(ethylene terephthalate), poly(ether sulfone), poly(vinylidene difluoride), or poly(tetrafluoroethylene).
8. The analyte indicator of claim 1, wherein the porous base is flexible.
9. The analyte indicator of claim 1, further comprising:
a second polymer unit attached or polymerized onto or out of the porous base; and
a second analyte sensing element attached to the second polymer unit or copolymerized with the second polymer unit, wherein the second analyte sensing element includes a second indicator polymer chain and second indicator molecules attached to the second indicator polymer chain.

\* \* \* \* \*